(12) United States Patent
Kraus et al.

(10) Patent No.: US 8,920,360 B2
(45) Date of Patent: *Dec. 30, 2014

(54) OPHTHALMIC SURGICAL SYSTEM AND CONTROL APPARATUS THEREFOR

(71) Applicant: Carl Zeiss Meditec AG, Jena (DE)

(72) Inventors: Martin Kraus, Huettlingen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/854,559

(22) Filed: Apr. 1, 2013

(65) Prior Publication Data

US 2013/0226072 A1 Aug. 29, 2013

Related U.S. Application Data

(63) Continuation of application No. PCT/DE2011/001776, filed on Sep. 24, 2011.

(30) Foreign Application Priority Data

Sep. 30, 2010 (DE) .......................... 10 2010 047 011

(51) Int. Cl.
*A61F 9/007* (2006.01)
*A61B 3/10* (2006.01)
*A61B 3/117* (2006.01)
*A61M 1/00* (2006.01)

(52) U.S. Cl.
CPC ............ *A61F 9/00745* (2013.01); *A61B 3/102* (2013.01); *A61B 3/1173* (2013.01); *A61M 1/0058* (2013.01)
USPC ............................................. 604/22; 604/67

(58) Field of Classification Search
CPC ... A61F 9/00736; A61F 9/00745; A61B 3/00; A61B 3/102; A61B 3/1173; A61M 2210/0612; A61M 1/0058; A61M 1/0062; A61M 1/0064; A61M 1/0023
USPC ...................................................... 604/22, 67
See application file for complete search history.

(56) References Cited

U.S. PATENT DOCUMENTS 5,700,240 A * 12/1997 Barwick et al. ................. 604/22
7,377,645 B2 * 5/2008 Wrobel et al. ................. 351/221

(Continued)

FOREIGN PATENT DOCUMENTS

WO WO 2007/121144 A1 10/2007

OTHER PUBLICATIONS

International Search Report dated Mar. 22, 2012 of international application PCT/DE2011/001776 on which this application is based.

(Continued)

*Primary Examiner* — Quynh-Nhu H Vu

(74) *Attorney, Agent, or Firm* — Walter Ottesen P.A.

(57) ABSTRACT

A control apparatus for an ophthalmic surgical system for phacoemulsification of an eye lens has an optical system for generating an object region wherein at least part of the eye lens and part of a needle of a phacoemulsification handpiece are arranged. The handpiece is provided with an aspiration line; an image evaluation unit is suitable for evaluating the generated image in such a way that an evaluation variable, dependent on an occlusion of the aspiration line, is determined, which is a kinematic measurement variable and/or a geometric measurement variable and/or an optical measurement variable of a particle, produced by emulsification, of the eye lens to be treated. A control unit, dependent on the evaluation variable supplied thereto, determines a control variable to control an absolute value of a parameter of the ophthalmic surgical system.

10 Claims, 6 Drawing Sheets

(56) References Cited

U.S. PATENT DOCUMENTS

2004/0152990 A1    8/2004  Mackool
2008/0319451 A1*  12/2008  Zacharias ................ 606/107
2009/0306581 A1*  12/2009  Claus ...................... 604/22
2011/0087156 A1*   4/2011  Claus et al. .............. 604/22
2013/0218168 A1*   8/2013  Hauger et al. ........... 606/107

OTHER PUBLICATIONS

English translation of the Office action of the German Patent Office dated Mar. 31, 2011 in German patent application 10 2010 047 011.2 on which the claim of priority is based.

* cited by examiner

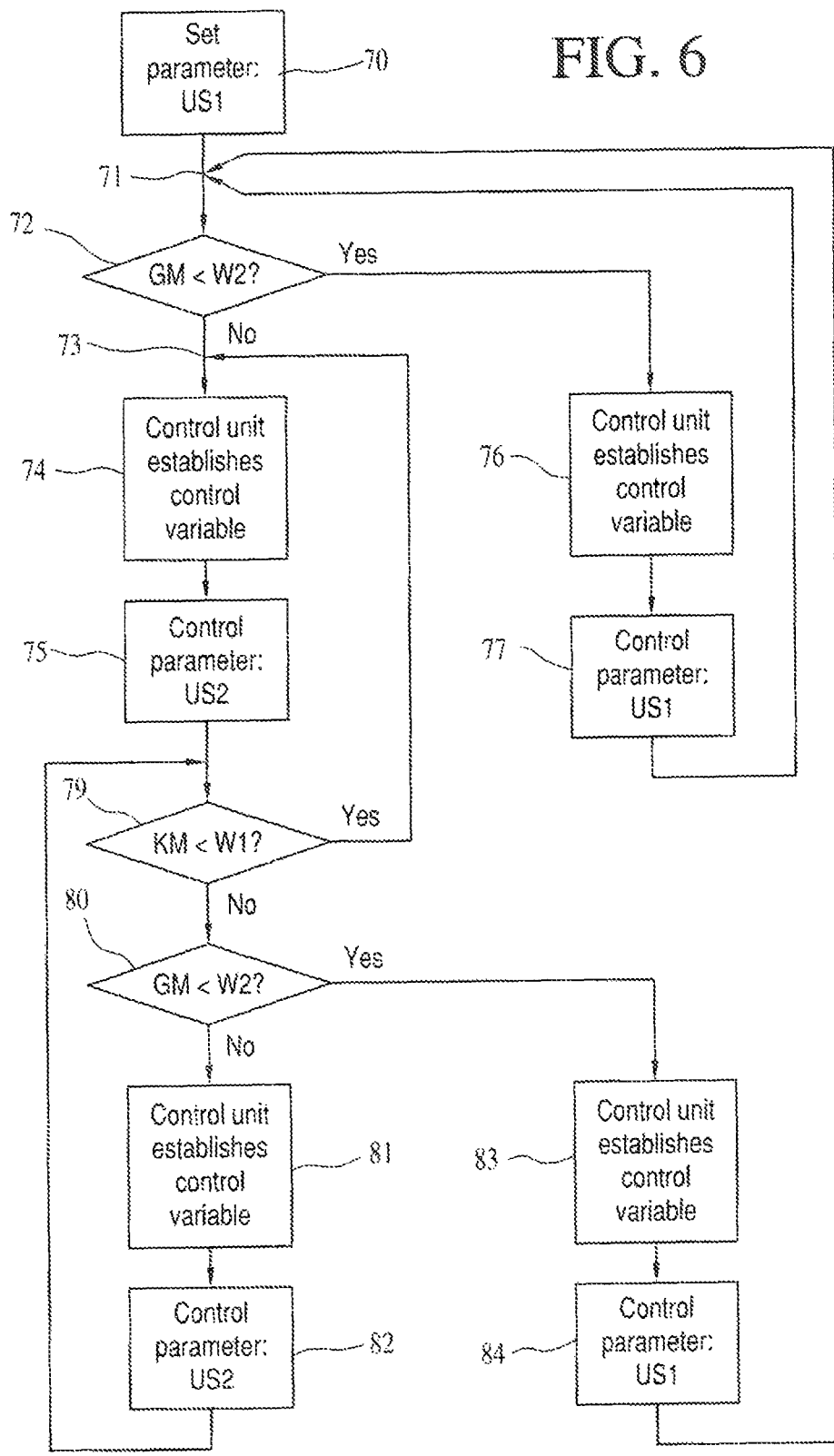

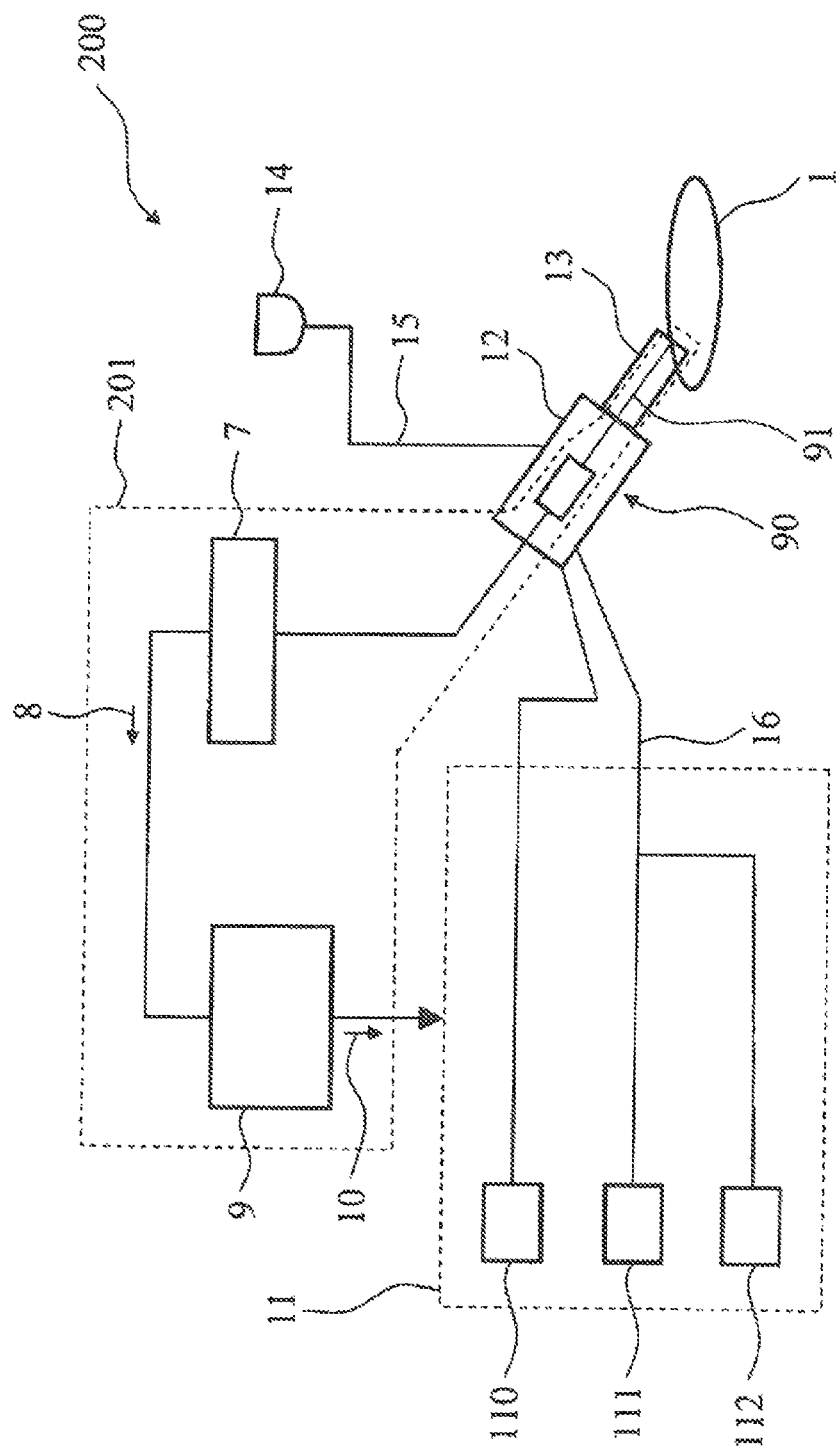

OPHTHALMIC SURGICAL SYSTEM AND CONTROL APPARATUS THEREFOR

CROSS REFERENCE TO RELATED APPLICATIONS

This application is a continuation application of international patent application PCT/DE2011/001776, filed Sep. 24, 2011, designating the United States and claiming priority from German application 10 2010 047 011.2, filed Sep. 30, 2010, and the entire content of both applications is incorporated herein by reference.

FIELD OF THE INVENTION

The invention relates to a control apparatus for an ophthalmic surgical system for phacoemulsification of an eye lens, and an ophthalmic surgical system with such a control apparatus.

BACKGROUND OF THE INVENTION

There are a number of surgical techniques for treating clouding within the eye lens, which is referred to as a cataract in medicine. The most common technique is phacoemulsification, in which a thin needle is introduced into the diseased lens and excited to vibrate by means of ultrasound. The vibrating needle emulsifies the lens in its direct vicinity in such a manner that the created lens particles can be suctioned away through a line by means of a pump. In the process, a rinsing fluid (irrigation fluid) is supplied, with the particles and the fluid being suctioned away through an aspiration line, which is usually arranged within the needle. Once the lens has been completely emulsified and removed, a new artificial lens can be inserted into the empty capsular bag, and so a patient treated in this manner can regain good visual acuity.

Surgery on the clouding within the lens or cataract surgery is an intervention with a relatively low rate of complications and high patient numbers. In Germany, approximately 600 000 operations are carried out each year, with the clouded lens being replaced by an artificial lens implant. However, the relatively low rate of complication can only be achieved if an operator with lots of experience carries out the operation. During the operation, it proves impossible to prevent a relatively large particle from positioning itself in front of the needle tip in such a way, while the lens is being broken up by means of a needle tip vibrating with ultrasound, that the needle tip or the suction opening thereof becomes blocked. This state is referred to as occlusion. In such a case, the suction pressure within the aspiration line increases substantially, with emulsification being interrupted at this time. Only once the particle has been removed again from the needle tip, for example as a result of a very high energy input, a significant increase in the suction pressure or a reversal of the aspiration pump running direction, can conventional suctioning away of the fluid and the small particles take place. At such a time, a blockage is therefore lifted, with the previously applied high negative pressure reducing instantaneously. The suction created thereby can lead not only to small particles and fluid being pulled toward the aspiration needle but also to part of the capsular bag coming into contact with the needle. The piercing of the capsular bag leads to significant complications for the patient; this needs to be avoided at all costs. An experienced surgeon has, over time, developed a sense for when an occlusion is just about to foe broken up. Nevertheless, there always is a risk of the patient's eye being injured.

SUMMARY OF THE INVENTION

It is an object of the invention to provide a control apparatus for an ophthalmic surgical system for phacoemulsification of an eye lens, in which the occurrence of an occlusion of a phacoemulsification needle and the break-up of such an occlusion at such a needle can be identified quickly and reliably such that there is a low risk of a patient's eye being injured. Furthermore, it is an object to develop an ophthalmic surgical system with such a control apparatus.

The control apparatus for an ophthalmic surgical system for phacoemulsification of an eye lens includes:

an optical system, by means of which an image can be generated of an object region, wherein at least part of the eye lens to be emulsified and part of a needle of a phacoemulsification handpiece with an aspiration line can be arranged in the object region;

an image evaluation unit, which is suitable for evaluating the generated image in such a way that at least one evaluation variable, dependent on an occlusion of the aspiration line, is established, which is a kinematic measurement variable and/or a geometric measurement variable and/or an optical measurement variable of a particle, produced by emulsification, of the eye lens to be treated; and, a control unit, by means of which, dependent on the at least one supplied evaluation variable, it is possible to establish a control variable, wherein the control variable can be used to control an absolute value of a parameter of the ophthalmic surgical system.

Hence, a parameter of the ophthalmic surgical system is therefore controlled by a control variable dependent on an evaluation variable which in turn is dependent on an occlusion in the aspiration line. This evaluation variable is established by means of an image generated by an optical system. Very fast image evaluation is possible by the use of an optical system.

According to the prior art, an occlusion is identified by recording pressure in the aspiration line. A relatively long period of time can pass until a pressure change at a needle reaches a pressure sensor, arranged downstream of the needle or even downstream of the phacoemulsification handpiece, in a console of an ophthalmic surgical system. A reaction initiated then by the ophthalmic surgical system to the detected change in pressure can often occur too late, and so it is not possible to avoid injuring the patient's eye. An image evaluation by means of an optical system requires no sluggish build-up of a pressure difference. Using the control apparatus according to the invention, it is now possible to capture the occurrence of an occlusion and the break-up of an occlusion more quickly than previously. Hence, in the case of an occlusion breach, it is possible to actuate a parameter of the ophthalmic surgical system more quickly and to reduce the risk of injury to the patient's eye.

According to the invention, the at least one evaluation variable of the image evaluation unit is a kinematic measurement variable and/or a geometric measurement variable and/or an optical measurement variable of a particle, produced by emulsification, of the eye lens to be treated. Here, the kinematic measurement variable can be the velocity or acceleration of the particle during a predetermined period of time. Hence, a particle is captured via the image evaluation unit in the image recorded by the optical system, wherein the velocity or the acceleration of this particle allows a statement to be made as to whether or not an occlusion is present. In the case of a very low velocity or acceleration, the particle is nearly or completely at rest, and therefore rests against the needle. As a result, it is possible to assume that an occlusion is present. In the case of a very high velocity or a high acceleration, the assumption can be made that the corresponding particle in front of the needle quickly passes into the suction opening of the aspiration line, and so an occlusion is either breaking up or not yet present, with this depending on what preceded this. If an occlusion was established beforehand, a high velocity or acceleration means a break-up of the occlusion. If an occlusion has yet to be established, a high velocity or acceleration of a captured particle in front of the needle means fast suctioning away, with there not yet being any risk to the patient's eye.

Alternatively, or in addition thereto, the at least one evaluation variable of the image evaluation unit can be a geometric measurement variable of a particle of the eye lens to be emulsified, which particle is situated in the direct vicinity of the tip of the needle. A geometric measurement variable can be an area or a circumference or a volume in the generated image of the particle to be emulsified. By way of example, if the area of the captured particle in front of a tip of the needle is so small that it can be expected that even the narrowest point within an aspiration line can be passed easily without a blockage occurring, a parameter or a plurality of parameters of the ophthalmic surgical system can be controlled in such a manner that suctioning away of particles and fluid, which is as quick as possible, is obtained. However, if the area is larger than, for example, the smallest cross section in an aspiration line, a blockage must be expected, and so a parameter of the ophthalmic surgical system is actuated accordingly in order, for example, to be able to quickly break-up the occlusion.

According to the invention, the at least one evaluation variable can be an optical measurement variable of a particle of the eye lens to be emulsified, which particle is situated in the direct vicinity of the tip of the needle. Here, an optical measurement variable can be a grayscale-value intensity or a color intensity. In an image to be evaluated, a large particle leads to stronger shadowing than a small particle, and so it is possible to deduce the size of the particle and the probability of an occlusion alone on the basis of a grayscale-value intensity or color intensity in the recorded image.

Depending on the evaluation variable, an absolute value of a parameter of the ophthalmic surgical system can be controlled by the control apparatus according to the invention. Such a parameter of the ophthalmic surgical system can be ultrasound energy supplied to the phacoemulsification handpiece, a suction power of an aspiration pump or a volumetric flow rate of a fluid for venting an aspiration line. If an occlusion in the process of breaking up is identified, ultrasound energy supplied to the phacoemulsification handpiece can be controlled down to a low absolute value. This reduces the stroke of the needle, and so relatively little energy is supplied to the eye. The absolute value of supplied ultrasound energy can then be set to be so low that further emulsification of an eye lens material is no longer possible. Alternatively, or in addition thereto, a parameter can also be a suction power of an aspiration pump. As soon as a breach of an occlusion is identified, the level of the built up negative pressure in the aspiration line can be reduced by reducing the suction pressure. The instantaneous lowering of the negative pressure after breaking up the occlusion then no longer starts at such a strong negative pressure. It is also possible that the conveying direction of the aspiration pump is reversed at this time such that there no longer is suction but pressing. This can significantly reduce the risk of, for example, the lens capsule being pulled to the needle and being pierced as a result of the strong negative pressure.

According to one embodiment of the invention, the at least one evaluation variable of the image evaluation unit can be a geometric measurement variable of a tissue surrounding the needle. By way of example, the geometric measurement variable can be a distance between the needle and a capsular bag. If the distance is smaller than a predetermined value, the control variable can be established by the control unit, in such a way that the ultrasound energy supplied to the handpiece is controlled to a minimal absolute value or to the value zero. Additionally, the aspiration pump can also be controlled in such a way that the negative pressure in the aspiration line reaches a lower value. This can reduce the risk of piercing a capsular bag as a result of a strongly vibrating needle tip or as a result of a strong negative pressure.

The optical system can have a light microscope and/or an OCT system. According to one embodiment of the invention, the optical system is at least in part arranged in the phacoemulsification handpiece. If the optical system is an OCT system, this OCT system can have: a source for temporally incoherent and spatially coherent light, a device for superposing laser radiation, which is radiated back into the sample beam path as a result of scattering centers in the lens tissue, with the laser radiation from a reference beam path such that an end reference signal and, therefrom, the position of scattering centers for the laser radiation can be established, and an image generation unit for generating an image. The OCT fiber can be arranged within or on the needle, wherein the fiber can have a rotating or scanning configuration in order to capture a volume region directly in front of the needle.

BRIEF DESCRIPTION OF THE DRAWINGS

The invention will now be described with reference to the drawings wherein:

FIG. 6 is a flowchart illustrating the influence of a kinematic measurement variable and a geometric measurement variable of a particle on a parameter of the ophthalmic surgical system; and, FIG. 7 is a schematic of a second embodiment of an ophthalmic surgical system with a control apparatus according to the invention.

DESCRIPTION OF THE PREFERRED EMBODIMENTS OF THE INVENTION

Figure 1:
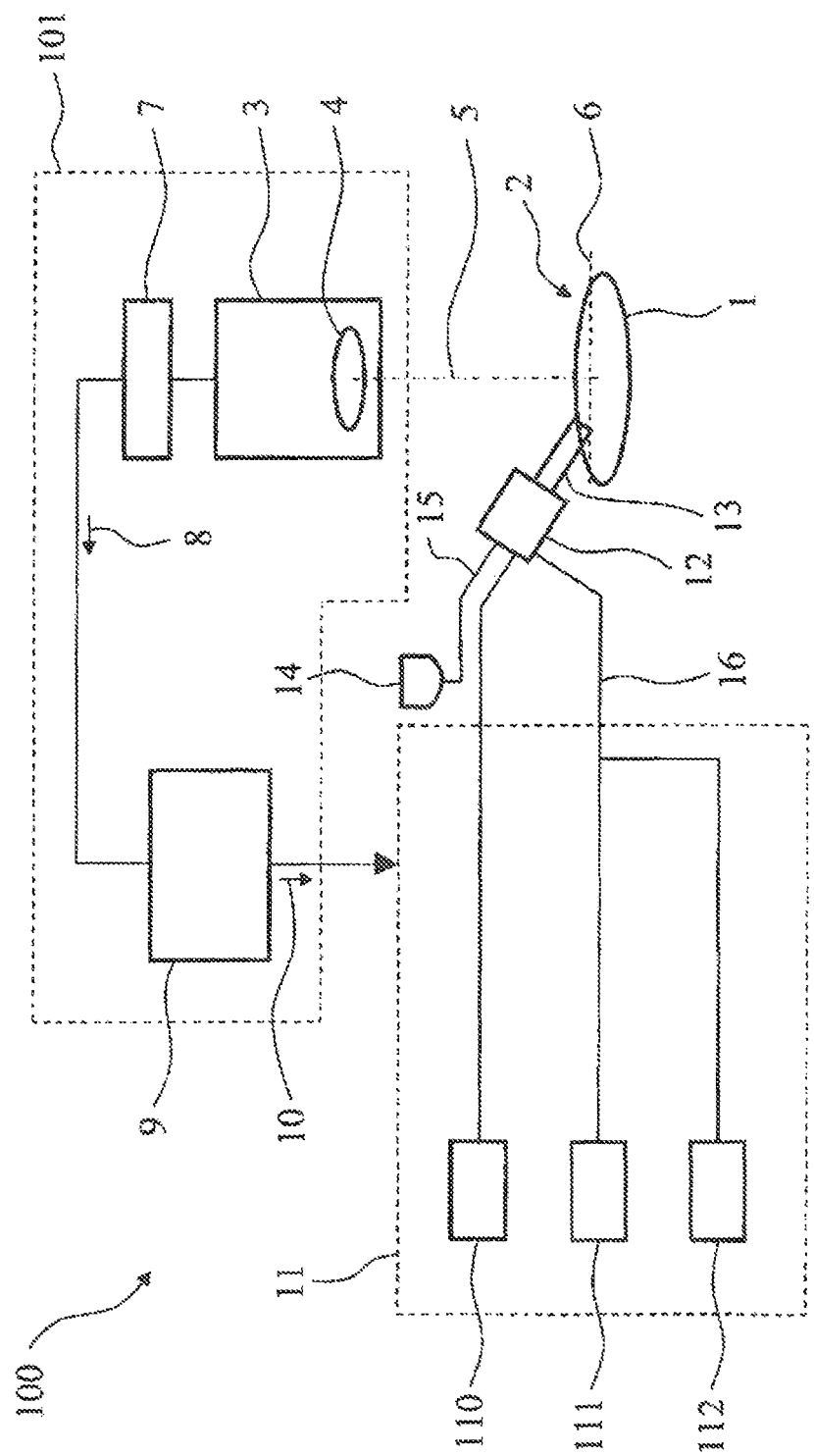
FIG. 1 is a schematic of an ophthalmic surgical system with a control apparatus according to a first embodiment of the invention.

FIG. 1 shows an ophthalmic surgical system 100 with a control apparatus 101. An eye lens 1 to be emulsified is arranged in an object region 2 of an optical system 3. In this embodiment shown in FIG. 1, the optical system 3 is a light microscope, with provision being made for a main objective 4 with an optical axis 5 and a focus plane 6. The focus plane 6 can be set within an object region 2. The optical system 3 has an image generation unit which generates an image that can be evaluated by an image evaluation unit 7. An evaluation variable 8 which can be fed to a control unit 9 can be established by the image evaluation unit 7. Depending on the evaluation variable 8, the control unit 9 can establish a control variable 10 which can act on a system component unit 11. The system component unit 11 can have an energy supply 110 for providing ultrasound energy for the needle 13 of a phacoemulsification handpiece 12. Alternatively, or in addition thereto, a system component unit 11 can have an aspiration pump 111, which suctions in fluid and emulsified particles from the eye lens through an aspiration line 16. A system component unit 11 can also have a reflux container 112, from which a fluid can be fed into the aspiration line 16 in order, in the case of an occlusion break-up, to influence the strong negative pressure in the aspiration line 16.

The system component unit 11 is coupled to a phacoemulsification handpiece 12 having a needle 13, with part of the aspiration line 16 usually being routed within the needle. An irrigation fluid is routed to the phacoemulsification unit 12 from an irrigation fluid container 14 through an irrigation fluid line 15 in order to provide sufficient amounts of irrigation fluid during the phacoemulsification. In addition to the aforementioned energy supply 110, the aspiration pump 111 or the reflux container 112, the system component unit 11 can also have other components which are suitable for influencing a parameter of an ophthalmic surgical system.

Figure 2:
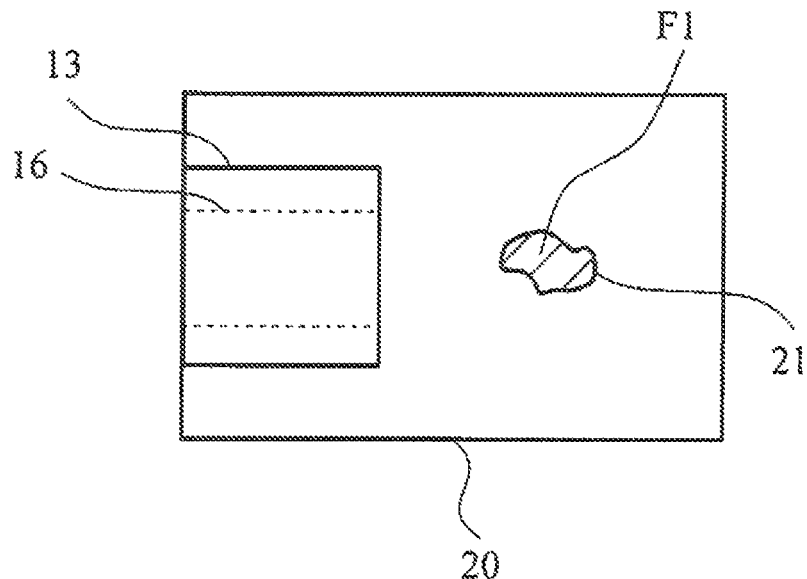
FIG. 2 shows an image from an image evaluation unit with part of a needle of a phacoemulsification handpiece and a relatively small particle.

FIG. 2 shows an image 20 of an image generated by the optical system 3, wherein this image 20 shows a front edge of a needle 13 of the phacoemulsification handpiece 12. Arranged within the needle 13 there is an aspiration line 16, which ends at the tip of the needle 13. A relatively small particle 21 with an area F1 is also shown. The area F1 of the particle 21 is so small that it is to be expected that even the narrowest cross section of the aspiration line 16 can be passed without this particle becoming stuck in the aspiration line 16. In the case of a particle 21 moving toward a needle 13 in such a manner, it is not expected that a blockage or occlusion of the aspiration line 16 occurs.

Figure 3:
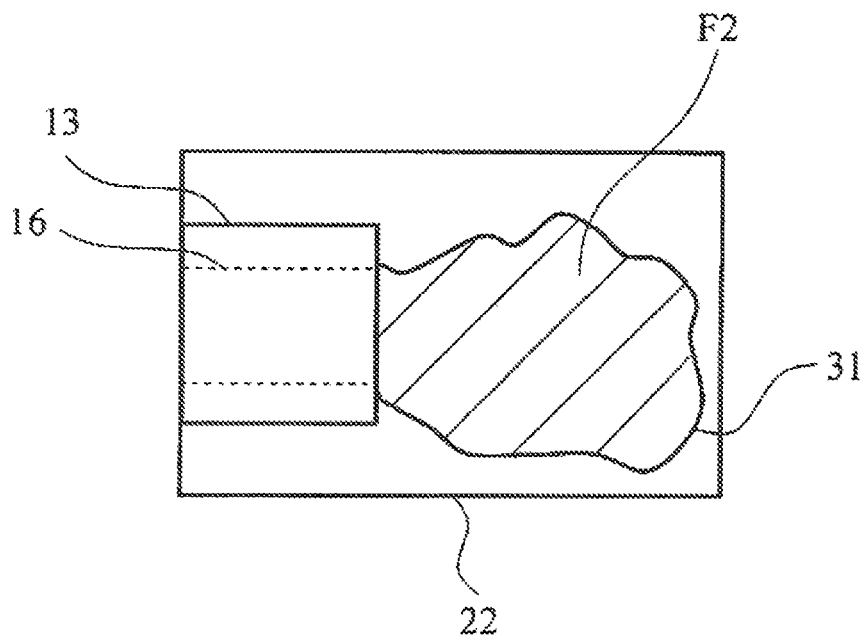
FIG. 3 shows an image from an image evaluation unit with part of a needle of a phacoemulsification handpiece with a relatively large particle.

FIG. 3 illustrates an image 22 from an image generation unit of the optical system 3, wherein the image 22 shows a needle 13 with an aspiration line 16 and a particle 31. The particle 31 has an area F2 which leads to the expectation that it cannot pass through the aspiration line 16. Hence a blockage of the aspiration line 16 must be expected. If the image generation unit generates such an image 22, the image evaluation unit 7 can identify, for example via a kinematic measurement variable, a geometric measurement variable or an optical measurement variable, that an absolute value of a parameter of the ophthalmic surgical system should be actuated in such a way that the effects of an occlusion or an occlusion break-up are reduced.

Figure 4:
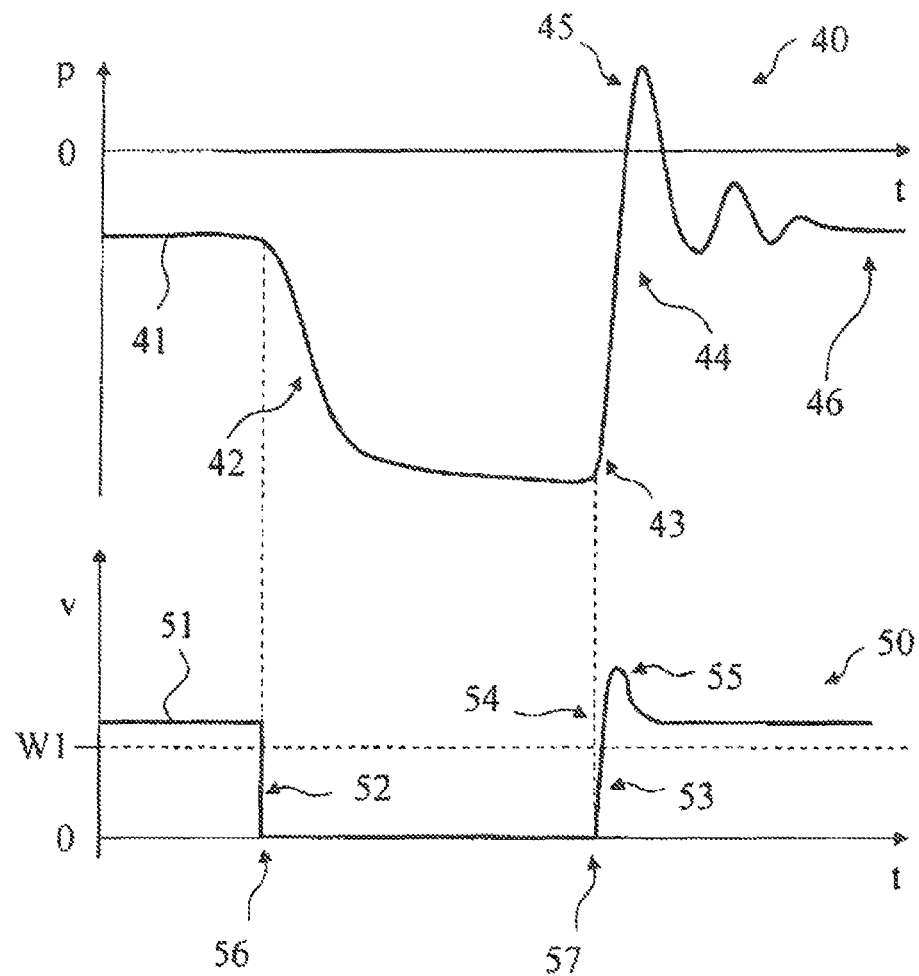
FIG. 4 is a diagram with a pressure profile and a diagram with an associated velocity profile of a particle of an eye lens in front of a needle of a phacoemulsification handpiece, plotted as a function of time.

FIG. 4 shows a diagram 40 of a pressure profile within an aspiration line plotted as a function of time. A first pressure can be applied at the beginning of a suction process as indicated by reference numeral 41. If a relatively large particle 31 blocks the needle 13, the pressure in the aspiration line greatly increases, see reference numeral 42. This high pressure remains until the occlusion breaks up, see reference numeral 43, with the negative pressure subsequently dissipating in a relatively short period of time, see reference numeral 44. As a result of the strong suction effect, the negative pressure can even transition into a positive pressure, see reference numeral 45, which subsequently zeroes in on an original pressure level again, see reference numeral 46.

A particle 31 causing such a pressure profile can have a velocity as shown in FIG. 4 in the lower diagram 50. During the normal suction process, see reference numeral 41, a particle can be suctioned toward the needle with a normal suction velocity 51. If an occlusion occurs, the velocity of the particle falls abruptly, see reference numeral 52, and so this particle only vibrates in front of a needle or remains completely stationary on the needle, see reference numeral 56. The absolute value of the velocity therefore drops below the absolute value of a previously set threshold W1, see FIG. 4. Such a change in velocity occurs very quickly and is a sign that an occlusion occurred. The velocity of the particle can remain very low in an unchanging manner during the occlusion until the occlusion is broken up. Only when the occlusion breaks up, see reference numeral 57, can the velocity of the smaller particles forming then increase again in front of the needle tip, see reference numeral 53, exceed the absolute value of the threshold W1 and then continue to rise, see reference numeral 54, until a maximum has been reached, see reference numeral 55, in order then to reduce slowly again to the value prior to the occlusion.

The velocity kinematic measurement variable of a particle therefore correlates immediately and directly with an occlusion within the aspiration line, wherein the absolute velocity or the velocity change of the particle can reliably identify the start of an occlusion and the breaking up of an occlusion. The advantage of capturing a velocity kinematic measurement variable compared to recording a pressure profile in an aspiration line is that, at the beginning of an occlusion, the velocity kinematic measurement variable changes much quicker from a high value to a lower one than a pressure change can set-in in an aspiration line. This can be explained by virtue of the fact that the resting particle in front of the needle is the cause of an occlusion, whereas the pressure change is the effect of an occlusion. If the cause can be established by an optical system, this leads to a faster detection of an occlusion than if the slowly building up pressure change is used for the control. This also applies conversely. If an occlusion breaks up, the velocity of the particles in front, of the needle changes very quickly. Although the pressure profile in the aspiration line also changes very quickly then, this is again only the result of the needle tip becoming free. The faster change in the velocity kinematic measurement variable compared to a pressure change and, additionally, capturing this kinematic measurement variable by means of an optical system renders it possible to capture an occlusion or an occlusion break-up significantly faster than was previously possible.

Figure 5:
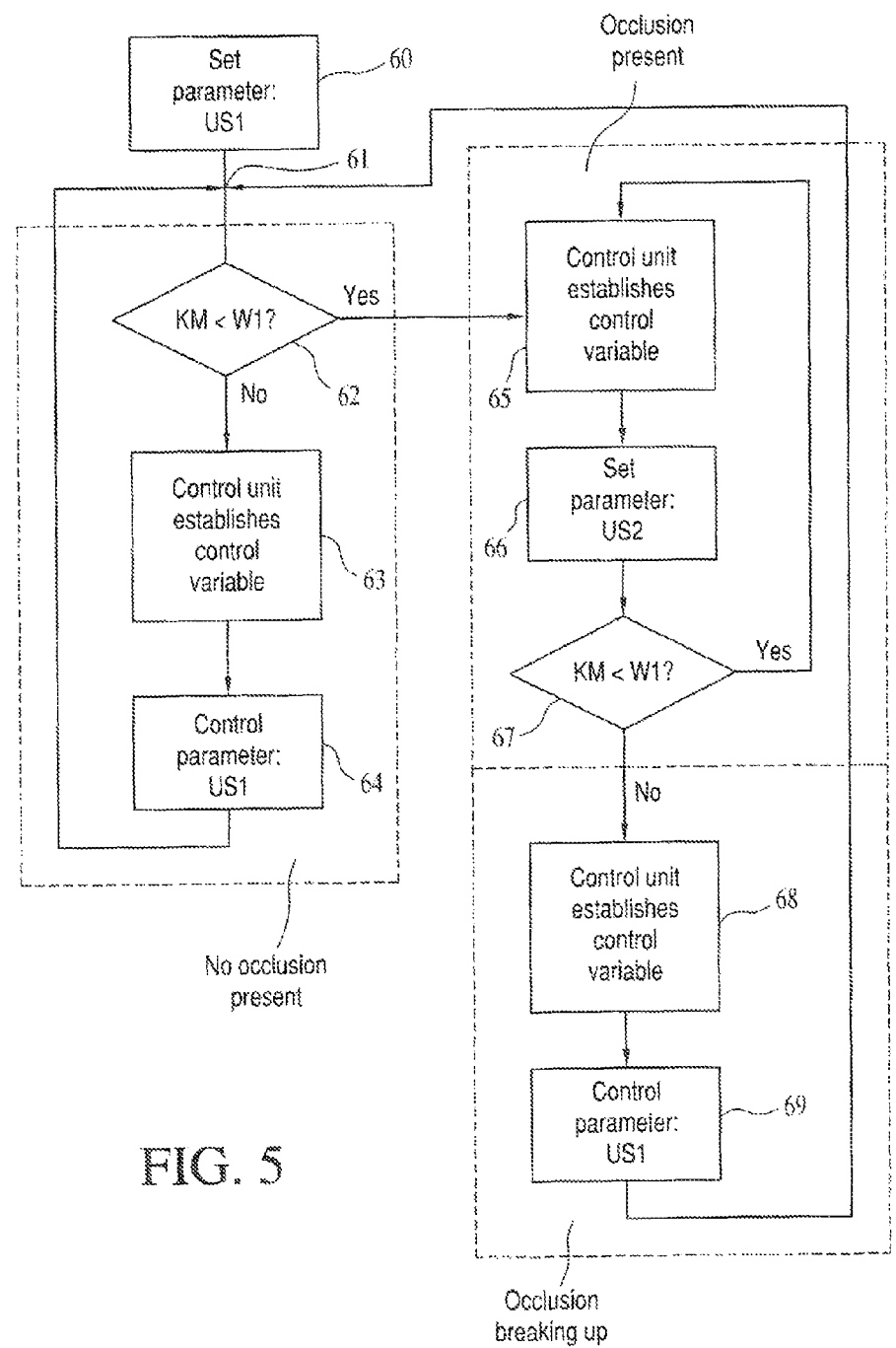
FIG. 5 is a flowchart which illustrates the influence of a kinematic measurement variable as evaluation variable on a parameter, of the ophthalmic surgical system, to be controlled.

FIG. 5 is a flowchart which is used to illustrate the interaction when capturing a kinematic measurement variable as evaluation variable and an associated parameter of an ophthalmic surgical system. Ultrasound energy, which is supplied to the phacoemulsification handpiece for emulsifying lens material, is selected as parameter of the ophthalmic surgical system. At the start, the ultrasound energy parameter is set to an absolute value US1, see reference numeral 60. This absolute value can be a relatively low energy, and so only little or no emulsification of lens material is achieved. If a kinematic measurement variable KM, for example a velocity of a particle, is selected as evaluation variable, it is subsequently possible to query whether this absolute value of the kinematic measurement variable KM is less than a threshold W1. If this does not apply, that is, if a particle moves with relatively high velocity, the control unit can establish a control variable therefrom, see box 63. The control variable can then be fed to a system component unit, for example an energy supply 110, such that the ultrasound energy parameter continues to remain set to the value US1, see box 64. Subsequently the query can return to a node point 61 again, wherein, as per query 62, there again is a query as to whether the kinematic measurement variable KM is less than the threshold W1.

If the kinematic measurement variable KM is less than the threshold W1, the particle clearly hardly moves or does not move at all, and so an occlusion is identified. From this, an image evaluation unit can generate an evaluation variable 8 which is fed to the control unit 9, which thereupon establishes an associated control variable 10, see box 65. The control variable 10 can then act on the ultrasound energy parameter in such a manner that a higher absolute value US2 is set, see box 66. It is therefore possible to apply higher ultrasound energy if an occlusion is present in order to break-up a clearly relatively large particle as quickly as possible. Subsequently, it is possible to query whether the current absolute value of the kinematic measurement variable KM is less than the threshold W1 again, see box 67. Thus, if the velocity of a particle still is relatively low and the absolute value thereof lies below the threshold W1, there clearly still is an occlusion and so the query is once again routed to box 65. In the case of the clearly present occlusion, the control unit 9 then again establishes an associated control variable 10, see box 65, such that a relatively high absolute value of the ultrasound energy US2 is set again, see Box 66. If it is identified during the subsequent query that the absolute value of the kinematic measurement variable KM is no longer less than the set threshold W1, the situation arises in which an occlusion is breaking up. The particle or particles are clearly starting to move with a relatively high velocity. In this case, the control unit 9 can establish an associated control variable 10, see box 68, and reset, the ultrasound energy parameter to a lower absolute value US1, see box 69. Hence the vibration of the needle can immediately be reduced to a lower absolute value when the occlusion is broken up. The method is subsequently continued at the node point 61 again, with there again being a query as to whether the magnitude of a kinematic measurement variable KM is less than the threshold W1, see box 62.

There is no occlusion in boxes 62, 63 and 64, an occlusion is beginning to be built up or continues to exist in boxes 65, 66 and 67, while an occlusion breaks up again in boxes 68 and 69. Hence, it is possible by capturing a kinematic measurement variable only to determine whether an occlusion is present or whether the occlusion is breaking up again.

FIG. 6 is a flowchart in which a kinematic measurement variable KM and a geometric measurement variable GM are used to control an ultrasound energy parameter. At the beginning, an ultrasound energy parameter is set to an absolute value US1, see box 70. Subsequently a query is made as to whether a geometric measurement variable GM is less than a threshold W2. By way of example, the geometric measurement variable can be an area of a particle. If the geometric measurement variable GM is less than the threshold W2, that is, if a relatively small particle is present, the evaluation unit determines an evaluation variable 8 which is fed to a control unit 9, which thereupon establishes an associated control variable 10, see box 76. Since the captured particle is small enough, there is no need for additional emulsification, and so the ultrasound energy parameter can remain set on the low absolute value US1, see box 77. Subsequently, the query can be returned, to the node point 71, and so there again is a query as to whether the geometric measurement variable GM is less than a threshold W2, see box 72.

However, if the geometric measurement variable GM is greater than the threshold W2, that is, if a relatively large piece is present in front of the needle 13, the evaluation unit determines an evaluation variable 8 which is fed to a control unit 9, which thereupon establishes an associated control variable 10, see box 74. The ultrasound energy parameter can then be set to a higher absolute value US2, see box 75. In this case, the ultrasound energy parameter can be changed from a low absolute value to a higher absolute value as the result of only capturing a geometric measurement variable. The higher absolute value US2 is expedient in this case because there is the risk in the case of a large particle that this particle cannot be routed through the aspiration line without blockage. A higher absolute value of energy can be used to break-up this large particle into smaller particles.

After setting the parameter to a higher absolute value US2, it is possible to query directly thereafter whether the kinematic measurement variable KM is less than the threshold W1. This checks whether, for example, a velocity of the identified particle is less than the threshold W1, see box 79. If this is not the case, that is, if the particle is moving at a relatively high velocity, it is possible to query directly thereafter whether a geometric measurement variable is less than a threshold W2, see box 80. If this applies and a particle is captured with a relatively high, velocity, the particle appears to swim in the fluid again.

By querying the geometric measurement variable, a check is made as to whether or not the particle was in fact emulsified into a plurality of smaller particles. If the geometric measurement variable is greater than a threshold W2, that is, if a large particle which merely moves backward and forward in front of the needle or tremors in front of the needle are still present and a blockage has still not been dissolved, the control unit establishes an associated control variable, see box 81. Since the particle still appears to be relatively large, the ultrasound energy parameter is still left on a high absolute value US2, see box 82, and so the relatively large particle can be emulsified into small particles. Subsequently the query returns to a node point 78 prior to the query as per box 79.

However, if during the query 80 of the geometric measurement variable it is identified that the geometric variable is less than a threshold, that is, that only small particle sizes are still present, the control unit 9 establishes an associated control variable 10, see box 83, and so the ultrasound energy parameter is set to a lower absolute value US1, see box 84. That is, if only relatively small particles are still present, it is no longer necessary to continue to introduce high ultrasound energy into the system. The small particles, present in that case, and the associated fluid can be suctioned away, without high energy continuing to be introduced into the system. Subsequently, the query can again be returned to the node point 71, and so a query is made again as to whether the geometric measurement variable GM is less than a threshold W2, see box 72. The process then continues as described above.

FIG. 7 shows a second embodiment of a control apparatus for an ophthalmic surgical system. The ophthalmic surgical system 200 has a control apparatus 201, which has an optical, system 90, an image evaluation unit 7 and a control unit 9. The optical system 90 can be present in the form of an OCT system, which has a source for temporally incoherent and spatially coherent light, additionally having a device for superposing laser radiation from a sample beam path with laser radiation from a reference beam path, and furthermore has an image generation unit for generating an image. The optical system 90 furthermore has an OCT fiber 91, which is arranged in the needle 13 or on the needle 13. The image generated by the image generation unit is thereupon routed to an image evaluation unit 7 which evaluates the image, with an evaluation variable 8 being established. This evaluation variable 8 can be fed to a control unit 9 which establishes a control variable 10. The control variable 10 can subsequently act on a system component unit 11 in order to control the absolute value of a parameter of the ophthalmic surgical system 200. By way of example, the system component unit 1 can have an energy supply 110, an aspiration pump 111 or a reflux container 112. The system component unit 11 is coupled to a phacoemulsification handpiece 12, and so the signal from the energy supply 110 for example can be used to actuate a phacoemulsification needle 13. The ophthalmic surgical system 200 furthermore has an irrigation container 14, from which, through an irrigation line 15, fluid can be routed to the handpiece 12 and from there to an eye lens 1 to be treated.

Furthermore, it is feasible that an ophthalmic surgical system has an optical system 3 in the form of a light microscope and an optical system 90 in the form of an OCT system.

According to a further embodiment, an OCT system can also be arranged within the light microscope, wherein such an OCT system can additionally be arranged within a handpiece.

It is understood that the foregoing description is that of the preferred embodiments of the invention and that various changes and modifications may foe made thereto without departing from the spirit and scope of the invention as defined in the appended claims.

What is claimed is:

1. A control apparatus for an ophthalmic surgical system for phacoemulsification of an eye lens to be treated, the ophthalmic surgical system having a parameter and including a phacoemulsification handpiece having a needle and an aspiration line, the control apparatus comprising:
   an optical system configured to generate an image of an object region wherein at least part of the eye lens to be emulsified and at least part of the needle are arranged;
   an image evaluation unit configured to evaluate said image such that at least one evaluation variable, which is dependent on an occlusion of said aspiration line, is determined;
   said evaluation variable being at least one of a kinematic measurement variable, a geometric measurement variable and an optical measurement variable of a particle of the eye lens generated by emulsification;
   a control unit configured to determine a control variable in dependence upon at least one of said evaluation variables; and,
   said control variable being configured to control a value of the parameter of the ophthalmic surgical system.

2. The control apparatus of claim 1, wherein said kinematic measurement variable is one of the velocity of the particle during a predetermined time duration and the acceleration of the particle during a predetermined time duration.

3. The control apparatus of claim 1, wherein the particle has a surface, a circumference and a volume, and wherein said geometric measurement variable is one of said surface, said circumference and said volume of said particle.

4. The control apparatus of claim 1, wherein said optical measurement variable is one of a gray-scale value intensity and a color intensity.

5. The control apparatus of claim 1, wherein said evaluation variable of said image evaluation unit is a geometric measurement variable of a tissue surrounding said needle.

6. The control apparatus of claim 1, wherein the ophthalmic surgical system further has an energy supply configured to supply the phacoemulsification handpiece with ultrasound energy, an aspiration pump having a suction power; and, said aspiration line is configured to have a volume fluid flow therein; and, said parameter of the ophthalmic surgical system is one of an ultrasound energy supplied to the phacoemulsification handpiece by said energy supply, said suction power of said aspiration pump and said volume fluid flow of a fluid for venting said aspiration line.

7. The control apparatus of claim 1, wherein said optical system includes at least one of a light microscope and an OCT system.

8. The control apparatus of claim 1, wherein said optical system is at least partially arranged in the phacoemulsification handpiece.

9. An ophthalmic surgical system for phacoemulsification of an eye lens to be treated, the ophthalmic surgical system having a parameter and comprising:
   a phacoemulsification handpiece having a needle and an aspiration line; and,
   a control apparatus including an optical system configured to generate an image of an object region wherein at least part of the eye lens to be emulsified and at least part of the needle are arranged; an image evaluation unit configured to evaluate said image such that at least one evaluation variable which is dependent on an occlusion of said aspiration line is determined; said evaluation variable being at least one of a kinematic measurement variable, a geometric measurement variable and an optical measurement variable of a particle of the eye lens to be treated generated by emulsification; a control unit configured to determine a control variable in dependence upon at least one of said evaluation variables; and, said control variable being configured to control a value of the parameter of the ophthalmic surgical system.

10. The ophthalmic surgical system of claim 9, further comprising:
   an energy supply configured to supply said phacoemulsification handpiece with ultrasound energy;
   an aspiration pump having a suction power;
   said aspiration line being configured to have a volume fluid flow therein;
   said fluid flow defining a volumetric flow rate; and,
   the parameter of the ophthalmic surgical system being one of said ultrasound energy supplied to said phacoemulsification handpiece by an energy supply, said suction power of said aspiration pump and said volume fluid flow of a fluid for venting said aspiration line.

* * * * *

UNITED STATES PATENT AND TRADEMARK OFFICE
CERTIFICATE OF CORRECTION

Page 1 of 1

PATENT NO. : 8,920,360 B2
APPLICATION NO. : 13/854559
DATED : December 30, 2014
INVENTOR(S) : Martin Kraus and Christoph Hauger It is certified that error appears in the above-identified patent and that said Letters Patent is hereby corrected as shown below:

In the Specification

In Column 1:
Line 66: delete "foe" and substitute -- be -- therefor.

In Column 6:
Line 39: delete "front," and substitute -- front -- therefor.

In Column 9:
Line 2: delete "1" and substitute -- 11 -- therefor.
Line 19: delete "foe" and substitute -- be -- therefor.

Signed and Sealed this
Ninth Day of June, 2015

Michelle K. Lee
*Director of the United States Patent and Trademark Office*